United States Patent [19]

Bluett

[11] Patent Number: 5,324,614
[45] Date of Patent: Jun. 28, 1994

[54] ERASE SETTING FOR COPIERS AND PRINTERS

[75] Inventor: Lynn J. Bluett, Rochester, N.Y.

[73] Assignee: Xerox Corporation, Stamford, Conn.

[21] Appl. No.: 937,572

[22] Filed: Aug. 31, 1992

[30] Foreign Application Priority Data

Aug. 2, 1991 [EP] European Pat. Off. ........ 91201999.9
Oct. 23, 1991 [EP] European Pat. Off. ........ 91202740.6

[51] Int. Cl.[5] .................................................. G03G 13/20
[52] U.S. Cl. ..................................... 430/124; 430/126; 430/97
[58] Field of Search ............... 430/124, 126, 19, 31, 430/97

[56] References Cited

U.S. PATENT DOCUMENTS

| | | | |
|---|---|---|---|
| 2,764,821 | 10/1956 | Buitenkant | 35/9 |
| 2,961,777 | 11/1960 | Neville et al. | 35/9 |
| 2,986,820 | 6/1961 | Neville et al. | 35/9 |
| 3,055,117 | 9/1962 | Bernstein et al. | 35/9 |
| 3,364,857 | 1/1968 | Lein et al. | 101/451 |
| 3,645,048 | 2/1972 | MacClaren | 51/281 |
| 3,877,155 | 4/1975 | Royka et al. | 35/9 R |
| 4,753,543 | 6/1988 | Mochimaru et al. | 400/119 |
| 5,017,432 | 5/1991 | Eddy et al. | 428/422 |

Primary Examiner—Steve Rosasco
Attorney, Agent, or Firm—Zosan S. Soong

[57] ABSTRACT

A method for printing or copying text and/or graphics on support medium in a removable manner to facilitate alterations comprising: creating a toned image, corresponding to the text and/or graphics on a support medium, wherein the image receiving side of the support medium prior to receiving the toned image is blank or contains extraneous markings; and fixing the toned image to the support medium by setting a fusing condition efficacious to removably fix the toned image, thereby rendering the first toned image removably fixed on the support medium.

12 Claims, 2 Drawing Sheets

ERASE SETTING FOR COPIERS AND PRINTERS

This invention relates generally to an electrostatographic copying or printing process and apparatus, and more particularly concerns a method and apparatus for rendering text and/or graphics entirely erasable by creating electrostatographically a toned image, corresponding to the text and/or graphics, which is removably fixed to a support material. Electrostatography includes electrophotography including xerography and electrography. Electrophotography employs a photosensitive medium to form, with the aid of electromagnetic radiation, an electrostatic latent charge pattern. Electrography utilizes an insulating medium to form without the aid of electromagnetic radiation, the electrostatic latent charge pattern. In the foregoing processes, the electrostatic latent image is developed with toner particles which are ultimately transferred to a sheet of support material. Hereinafter, the present invention will be illustrated in the context of electrophotographic printing processes and machines, but it is to be understood that the present invention is also suitable in electrographic processes and apparatuses, and the like.

Presently, alterations to documents such as engineering and architectural blueprints can be made by the use of correction liquid/tape or erasable vellum paper. However, qualifying erasable vellum paper for use in an electrostatographic machine is time consuming and expensive. Moreover, alterations over correction liquid/tape may not provide optimum results since the surface of the substrate is no longer uniformly smooth. In addition, application of the correction liquid/tape may be time consuming. Consequently, there is a need for processes to make changes to documents without the use of correction liquid/tape or erasable vellum paper.

Royka et al., U.S. Pat. No. 3,877,155, the disclosure of which is totally incorporated by reference, discloses the preparation of a responsive answer sheet containing both permanent meaningful information and removable confusing information by a two run process. First, the support sheet is routed through a xerographic imaging machine wherein permanent meaningful information is imprinted thereon. The meaningful information is permanently fixed to the transfer sheet in one embodiment by regulating the amount of heat energy absorbed by the toner from a resistance wire heat fixing device. The same support sheet containing the permanent information is redirected through the xerographic imaging machine and removable, confusing information is placed thereon by xerographic techniques with the sole change generally being that the fusing mechanism in the machine is changed from the first run and precisely controlled so that the transfer toner image becomes affixed to the support sheet in a removable manner.

The present invention differs from Royka et al., U.S. Pat. No. 3,877,155, in for example at least two aspects. First, in the present invention, the text and/or graphics is rendered entirely erasable on the support sheet. In contrast, in Royka et al., only a portion of the information on the support sheet is rendered removable. Second, in the present invention in embodiments, each support sheet undergoes only a single imprinting run to copy or to print thereon the text and/or graphics and accordingly the image bearing side of the support sheet prior to receiving the removable toned image is either blank or contains extraneous markings. Extraneous markings as used herein refers to company logos, letterheads, borders, title and revision blocks, and the like which are not part of the original text and/or graphics. In contrast, in Royka et al., each support sheet undergoes two imprinting runs to imprint thereon in succession first the permanent meaningful information and second the removable confusing information. Thus, placing the text and/or graphics on a single support medium requires a single imprinting run in the present invention, whereas Royka et al., requires two imprinting runs to place the required information on a single support medium. Another distinction is that in embodiments of the present invention, the instant method involves the additional steps of altering the support sheet containing the removable toned image and then making a permanently fixed copy of the altered sheet on a separate support sheet. In contrast, in Royka et al., the permanent information and the removable information are imprinted on the same support sheet. It is understood that the text and graphics may contain company logos, letterheads, borders, title and revision blocks, and the like but these are not considered extraneous markings since they are part of the original information.

The following prior art may also be relevant to various aspects of the present invention: Buitenkant, U.S. Pat. No. 2,764,821; Neville et al., U.S. Pat. No. 2,961,777; Neville et al., U.S. Pat. No. 2,986,820; Bernstein et al., U.S. Pat No. 3,055,117; Lein et al., U.S. Pat. No. 3,364,857; MacClaren, U.S. Pat. No. 3,645,048; Mochimaru et al., U.S. Pat. No. 4,753,543; and Eddy et al., U.S. Pat. No. 5,017,432.

SUMMARY OF THE INVENTION

It is an object of present invention to provide a method for creating removably fixed toned images.

It is another object in an embodiment of the present invention to provide a method for creating removably fixed toned images, wherein the removable toned images may be altered, and a subsequent electrostatographic copy of the altered toned image may be made on a separate support sheet.

It is a further object to provide in embodiments of the present invention a method and apparatus for creating a removably fixed toned image by setting a fixing condition different from that for creating a permanently fixed toned image.

It is an additional object to provide in embodiments of the present invention a method and apparatus for creating a removably fixed toned image by setting a fusing temperature and/or fusing pressure lower than that required to permanently fix a toned image to a support sheet.

It is still a further object to provide a method for altering documents containing text and/or graphics, and including letters, memorandums, reports, engineering and architectural blueprints, scientific drawings, and the like without the use of erasable paper and/or correction liquid/tape.

These objects and others are provided by a method for printing or copying characters on support medium in a removable manner to facilitate alterations comprising:

(a) creating a first toned image, corresponding to the characters on a first support medium, wherein the image receiving side of the first support medium prior to receiving the first toned image is blank or contains extraneous markings; and (b) fixing the first toned image to the first support medium by setting a fixing condition efficacious to removably fix the first toned image, thereby rendering the first toned image removably fixed on the first support medium. As used herein in embodiments, the term characters comprises text and/or graphics.

In embodiments the text and/or graphics to be printed or copied on support medium in a removable manner may be in the form of electronically or magnetically stored information, in the form of a hard copy which can be electrostatographically copied as described herein, and the like. The text and/or graphics may not fit onto a single support sheet and accordingly may be copied or printed onto a plurality of support sheets, each sheet undergoing a single imprinting run to place thereon a removably fixed toned image. In an embodiment of the present invention, a permanently fixed electrostatographic copy of the sheets containing the removably fixed toned images, optionally altered, may be made by producing a like number of support sheets containing permanently fixed toned images. Each support sheet containing the permanently fixed toned images undergoes a single imprinting run to place thereon the permanently fixed toned images.

The extraneous markings may be placed on the support sheet by electrostatographic methods or by non-electrostatographic methods including letterpress, lithography, or gravure, and the like. In a preferred embodiment, the extraneous markings do not overlap with the toned image corresponding to the text and/or graphics.

DESCRIPTION OF THE PREFERRED EMBODIMENTS

Figure 1:
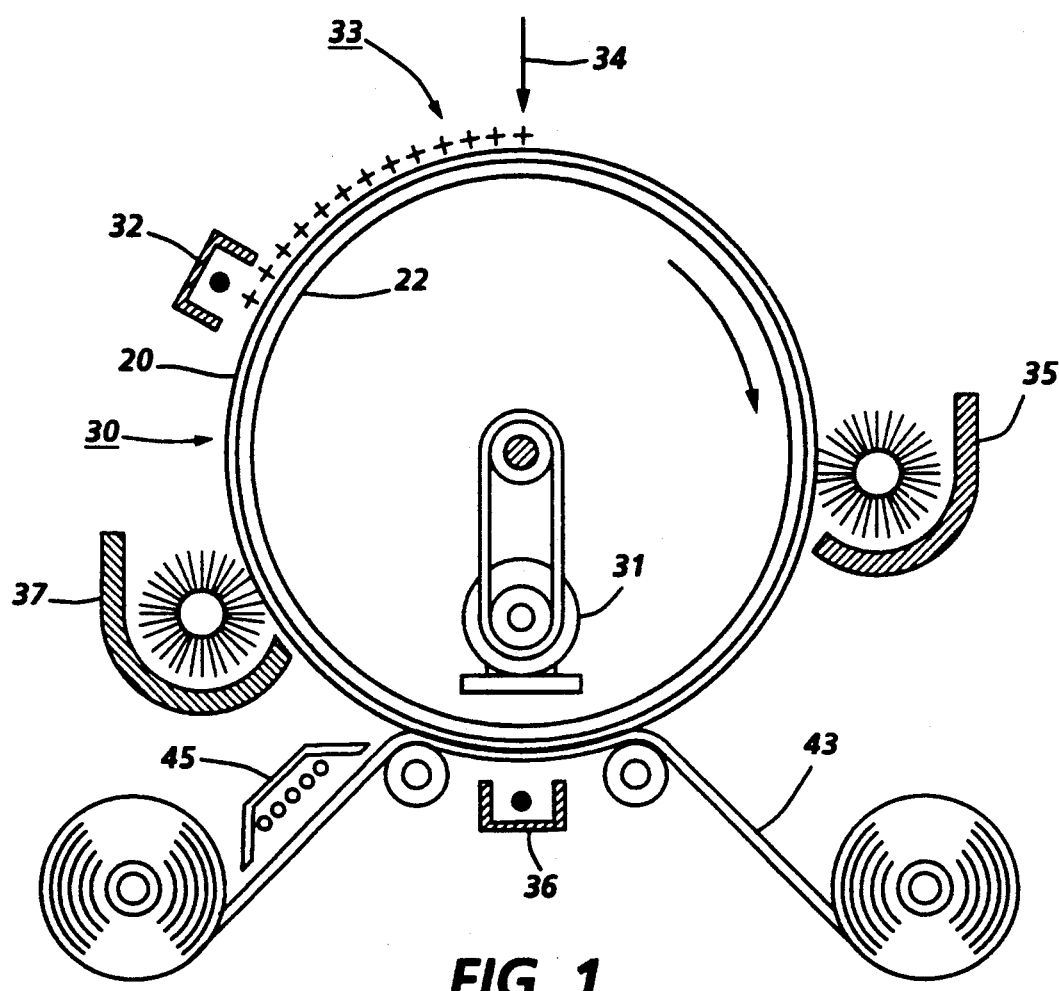
FIG. 1 is a partially schematic illustration of a xerographic imaging device which is the preferred mode of carrying out the present invention.

Referring now to FIG. 1, there is shown a schematic illustration of an embodiment of an automatic xerographic copying apparatus, wherein a xerographic plate comprising a photoconductive layer 20, for example, comprising amorphous selenium, zinc oxide, cadmium sulfide, selenium/tellurium, or selenium/tellurium/arsenic, and the like in a binder on a conductive substrate 22 in the form of a drum 30 is rotated by a motor 31 and sequentially passes a sensitizing station 32 illustrated as a corona discharge device depositing illustratively positive charge on the plate, an exposure station 33 where an optical image illustrated by light ray 34 is projected onto the surface of the charged drum, a developing station 35 depicted as a brush development device, a transfer station 36 illustratively using a corona device for electrostatic transfer and cleaning station 37 depicted as a brush cleaning device.

At exposure station 33, the imagewise illuminated areas of the drum become more electrically conductive and at least partially discharge the surface of drum 30 in said areas to thereby create a latent electrostatic image corresponding to the optical image which is rendered visible or developed at developing station 35 and then transferred to a transfer web at transfer station 36. The transferred image on web 43 is fixed at fixing station 45 depicted as a heat fixing device. After transfer of the image, residual developer is removed from the xerographic drum surface at cleaning station 37 and the drum is then resensitized by corona charging at sensitizing station 32 to prepare it for another imaging cycle. In another embodiment, the latent image alternatively may be recorded by exposing the charged surface to controlled laser emissions in a raster output scanner system.

The latent electrostatic image may be rendered visible or developed by contacting the latent image areas with toner in single or two component development. Any suitable developing method may be used including cascade development illustrated in U.S. Pat. No. 4,015,561; magnetic brush development illustrated in U.S. Pat. No. 3,967,892; fur brush development illustrated in U.S. Pat. No. 3,841,265; liquid electrophoretic development illustrated in U.S. Pat. No. 4,935,788; scavengeless development illustrated in U.S. Pat. No. 5,053,824; and jumping development illustrated in U.S. Pat. No. 4,660,059, the disclosures of all of the above being totally incorporated by reference.

One of the advantages of the xerographic process which renders it particularly adapted to the practice of the present invention is that, at fusing station 45, the toner image may be permanently printed or fused into transfer material 43 or may be removably fused thereto by regulating the parameters of the fixing process.

In FIG. 1, a resistance wire heat fixing unit is used and semi-permanent or removable fixing is accomplished by controlling the total heat energy supplied to the surface of the support medium and the toner so that only a sufficient fusing takes place to essentially tackify toner particles to the support medium without at the same time causing the particles to collect into a uniform mass and to become at least partially absorbed into the support medium which would result upon calling in, what is known in the art, as a permanent xerographic image and one which may not be readily abradably removed by using ordinary techniques. Where fixing is accomplished in the accordance with present invention, the removably imprinted toned image or portions thereof may be removed with relative ease by, for example, rubbing a response area with an ordinary pencil eraser or by scraping with a knife or blade or other suitable abrading means.

The support material containing the removably fixed toned image may be altered by erasing a portion of the toned image, marking with a writing device, or both. A copy of the resulting altered document may be made on a separate support sheet by conventional electrostatographic techniques and permanently affixed thereto by any suitable fixing method. In one embodiment, the permanently fixed toned image copy is made in the same electrostatographic apparatus as used to produce the removably fixed toned image with the primary change being that the fusing temperature is set so as to permanently fuse the toned image to the support sheet. For example, a toned image may be permanently fixed to the support sheet by regulating the amount of heat energy absorbed by the toner from the resistance wire heat fixing device illustrated in FIG. 1, and more specifically described in Eichler, U.S. Pat. No. 2,965,868, the disclosure of which is totally incorporated by reference. It is understood that the permanently fixed toned image copy of the altered document containing the removable toned image may be made in a different electrostatographic device which may be a conventional device wherein the fixing system is set only to permanently fix toned images.

The degree of permanentness of a xerographic toner image has been classified in a variety of ways in the art including the class 1 through class 4 degrees used in Insalaco, U.S. Pat. No. 3,130,064 wherein a class 1 fix is where the toner particles rest on the surface as discrete unglazed particles of powder, a minor degree of melting has taken place only to the extent that surface irregularities in the toner particles have been smoothed out; a class 2 fix is one wherein the toner particles are glazed but still exist as separate particles on the image support member; a class 3 fix is one wherein the electroscopic toner particles are glazed and wherein the affected particles have lost their boundaries, that is they have merged together and to the surface of the support member by being partially absorbed therein; and a class 4 fix is wherein the toner particles have so merged and penetrated the support material that the separate fibers of support material can be seen through the fused toner particles. For most commercial applications of xerography a class 3 fix is adequate, although in many instances a class 4 fix is actually accomplished.

Thus, in embodiments of the present invention, permanently fixed toned images typically will be fixed to a class 3 or higher degree of fix. Removably fixed toned images typically will be fixed to less than a class 3 fix and preferably in the range of from a class 1 fix to a class 2 fix, inclusively. In this range, the toner particles have been sufficiently heated so that a minor degree of melting has occurred, sufficient to tackify the individual particles to the substrate or portions of the permanently printed image and also sufficient to achieve some minor tackification between individual toner particles at their points of mutual contact. However, the individual particles have not in general lost their individual boundaries and started to flow together into a smooth coalesced mass. Thus, in embodiments of the present invention, the removable toned images may be below the stage of a class 3 fix. Under such circumstances, removably fixed particles may be removed by merely supplying sufficient energy to disrupt the tackification bonds between individual particles and the substrate. Typically such energy may be supplied by merely abrading the particles with a conventional eraser. Alternatively, however, a mild solvent such as, for example, trichlorethane, in which conventional toner compositions such as that described in Example 1 of Insalaco, U.S. Pat. No. 2,892,794 are slightly soluble, may be applied as for example with a fabric-tipped instrument or the like. In embodiments, the removable toned image may be completely removed or partially removed.

Although the method of heat fusing has been particularly described herein, any suitable method of fixing and regulating the fix of a xerographic image may be used. Typical fixing means which may be readily adapted either alone or in combination with other methods specified herein, to practice the invention include: infra-red heating sources as described in Roshon, U.S. Pat. No. 2,807,793 and Allen et al., U.S. Pat. No. 2,807,704; the combination of heat and pressure as illustrated in Carlson, U.S. Pat. No. 2,990,278 and Aser et al., U.S. Pat. No. 3,291,466; the vapor plus pressure fixing as described by Walkup, U.S. Pat. No. 2,995,085; or solvent vapor alone as described in Greaves, U.S. Pat. No. 2,726,166, the disclosures of all of the foregoing are totally incorporated by reference, and others. One method of fixing may be used to fix permanent information and a different method to fix the removable information, with the fixing means to fix the permanent information being chosen to give a deeper toner penetration into the support surface such as solvent fixing or oven fusing with the removable information being fixed by low temperature pressure rollers which would adequately fix the toner but be more subject to removal from the support sheet than the permanent information since fiber penetration would be less. Another way of controlling the degree of fix is to use toners of varying melting points, for example, using a crystalline toner in combination with a heat-pressure fixing means with the toner heated below its melting point to removably fuse and the heated roller heated sufficiently to raise the toner above the melting point to permanently fuse.

Any effective temperature may be employed to permanently fix toner to the support material. Typically, the toner particles are permanently fused to the substrate by heating to a temperature of between about 90° C. to about 160° C. or higher depending upon the softening range of the particular resin used in the toner. It is undesirable, however, to raise the temperature of the substrate substantially higher than about 200° C. because of the tendency of the substrate to discolor at such at elevated temperatures particularly when the substrate is paper. A preferred permanent fusing temperature ranges from about 100° C. to about 160° C. Any effective temperature may be employed to removable fix toner to the support material. It is preferred that the removable fixing temperature ranges from about 40° C. to about 90° C., and more preferably from about 50° C. to about 70° C.

Alternative fixing methods that may be employed in the present invention will now be discussed in more detail. These methods include providing the application of heat and pressure substantially concurrently by various means: a roll pair maintained in pressure contact; a belt member in pressure contact with a roll; and the like. Heat may be applied by heating one or both of the rolls, plate members or belt members. The fusing of the toner particles takes place when the proper combination of heat, pressure and contact time are provided. The balancing of these parameters to bring about the fusing of the toner particles can be effected to suit particular machines or process conditions.

Fuser members, release agents and fusing systems are described in U.S. Pat. No. 4,264,181 to Lentz et al., U.S. Pat. No. 4,257,699 to Lentz and U.S. Pat. No. 4,272,179 to Seanor, the disclosures of which are totally incorporated by reference. These patents describe fuser members and methods of fusing thermoplastic resin toner images to a substrate wherein a polymeric release agent having functional groups is applied to the surface of the fuser member. The fuser member comprises a base member having an elastomeric surface with a metal containing filler therein which has been cured with a nucleophilic addition curing agent. Exemplary of such fuser member is an aluminum base member with a poly(-vinylidenefluoride-hexafluoropropylene) copolymer cured with bisphenol curing agent having lead oxide filler dispersed therein and utilizing a mercapto functional polyorganosiloxane oil as a release agent. In those fusing processes, the polymeric release agents have functional groups (also designated as chemically reactive functional groups) which interact with the metal containing filler dispersed in the elastomer or resinous material of the fuser member surface to form a thermally stable film which releases thermoplastic resin toner and which prevents the thermoplastic resin toner from contacting the elastomer material itself. The metal oxide, metal salt, metal alloy or other suitable metal compound filler dispersed in the elastomer or resin upon the fuser member surface interacts with the functional groups of the polymeric release agent. Preferably, the metal containing filler materials do not cause degradation of or have any adverse effect upon the polymeric release agent having functional groups. Because of this reaction between the elastomer having a metal containing filler and the polymeric release agent having functional groups, excellent release and the production of high quality copies are obtained even at high rates of speed of electrostatographic reproducing machines.

The preferred elastomers are the fluoroelastomers and the most preferred fluoroelastomers are the vinylidenefluoride based fluoroelastomers which contain hexafluropropylene and tetrafluoroethylene as comohomers. Two of the most preferred fluroelastomers are (1) a class of copolymers of vinylidenefluoride and hexafluoroproplyene known commercially as Viton A and (2) a class of terpolymers of vinylidenefluoride, hexafluoropropylene and tetrafluoroethylene known commercially as Viton B. Viton A and Viton B and other Viton designations are trademarks of E. I. DuPont deNemours and Company. Other commercially available materials include Fluorel of 3M Company, Viton GH, Viton E60C, Viton B 910, and Viton E 430. The preferred curing system is a nucleophilic system with a bisphenol crosslinking agent to generate a covalently cross-linked network polymer formed by the application of heat following basic dehydrofluorination of the copolymer. The nucleophilic curing system also includes an organophosphonium salt accelerator. Some of the commercially available fluoroelastomer polymers which can be cured with the nucleophilic system are Viton E 60C, Viton B 910, Viton E 430, Viton A, Viton B. Example 4 of both U.S. Pat. Nos. 4,264,181 and 4,272,179 exemplify Viton B, an elastomer of poly(vinylidenefluoride-hexafluoropropylene-tetrafluoroethylene) with copper particles exhibiting excellent release of the thermoplastic resin toner when used with the mercapto functional polyorganosiloxane oil release agent. Example 3 in U.S. Pat. No. 4,257,699 has similar results with a bisphenol cure system. Unsatisfactory fusing results were achieved in Example 7 of U.S. Pat. No. 4,264,181 and 4,272,179 as well as Example 6 of U.S. Pat. No. 4,257,699 wherein Viton GH a terpolymer of poly(vinylidenefluoride-hexafluropropylene-tetrafluoroethylene) having a copolymerized cure site monomer and containing trace amounts of metal containing filler was cured with an aliphatic peroxide curing agent. Example 12 in U.S. Pat. No. 4,272,179 and 13 in U.S. Pat. No. 4,257,699 illustrate a similar fuser roll also cured with a conventional aliphatic peroxide curing agent and containing substantial quantities of lead oxide.

The elastomer having metal-containing filler dispersed therein may be in any effective thickness. Generally, where the fuser member is heated by internal means, the elastomer having metal oxide filler therein is preferably of such thickness as to constitute a minimal thermal barrier to heat radiating from inside the fuser member to the outermost layer of elastomer having metal oxide filler therein. Recommended thicknesses are generally greater than 0.5 rail (0.00127 cm), but may be from 1 rail (0.0025 cm) to about 200 mils (0.5 cm), the most preferred ranges being from about 4 mils (0.01 cm) to about 100 mils (0.25 cm). The preferred thickness depends upon the fuser member configuration and the particular backup or pressure member (hard or conformable) being used with the fuser member.

Any suitable polymeric release material having functional groups may be employed. Typical polymeric release agents are described in U.S. Pat. No. 4,101,686 which describes polyorganosiloxane fluids as release agents. The polyorganosiloxane fluids and other polymer fluids having functional groups interact with the metal oxide particles in the fuser member in such a manner as to form an interfacial barrier at the surface of the fuser member while leaving an unreacted low surface energy release fluid as an outer layer film. Other exemplary polymeric release agents having functional groups are described in U.S. Pat. Nos. 4,046,795, 4,029,827 and 4,011,362, the disclosures of which are totally incorporated by reference. The polymeric release agent having functional groups thereon may be found as a liquid or solid at room temperature but it is a fluid at operating temperatures. In preferred embodiments, the chemically reactive groups of polymeric release material are mercapto, carboxy, hydroxy, isocyanate, epoxy, and amino. The most preferred polymeric release agents having functional groups thereon used in accordance with the present invention are the mercapto functional polyorganosiloxanes described in U.S. Pat. Nos. 4,101,686 and 4,029,827, the disclosures of which are totally incorporated by reference.

In the embodiment where a roller pair, comprised of a fixing roller and a pressure roller, is maintained in contact, wherein one or both rolls are heated, the fixing pressure between the rolls optionally may be rendered adjustable. Electrostatic printing apparatuses with heated adjustable pressure toner fixing rolls are known, reference for example, Mochimaru et al., U.S. Pat. No. 4,753,543, the disclosure of which is totally incorporated by reference.

Figure 2:
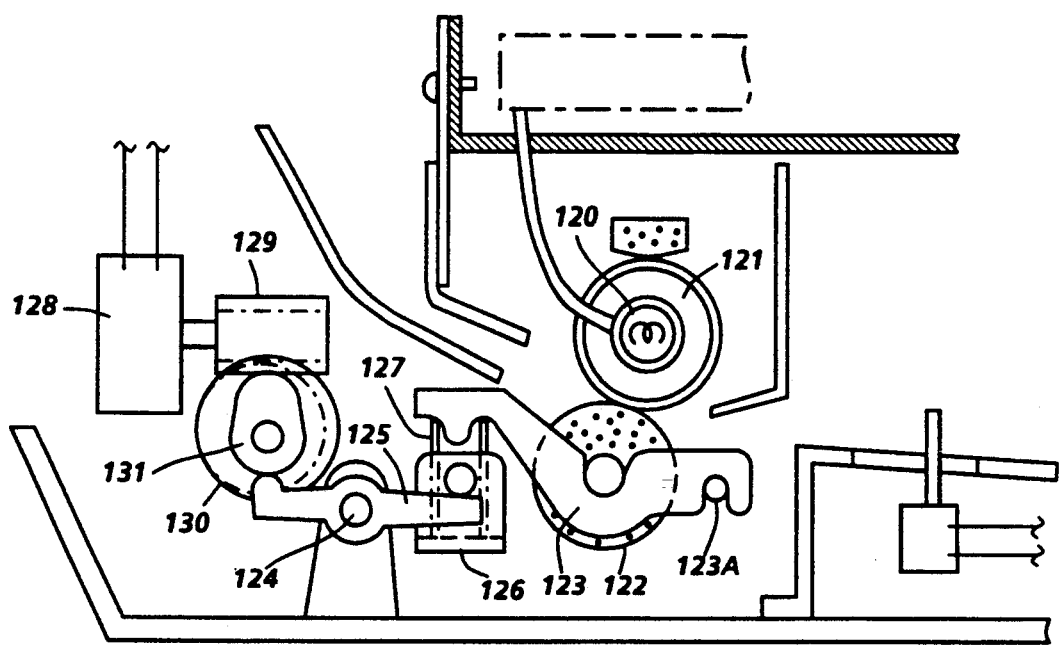
FIG. 2 is a partially schematic illustration of an alternative fixing system of an electrostatic printing apparatus with heated adjustable pressure toner fixing rolls.

In one embodiment as illustrated in FIG. 2, the fixing pressure may be rendered adjustable by providing a fixing roller 121, having a heater 120, which is journalled in bearings at a given position in an upper unit of a printing apparatus, and both ends of a pressure roller 122 are supported with levers 123. The printing apparatus comprises a lower unit and an upper unit that are joined at their backsides to form a clamshell design. One end of the lever 123 is rotatably supported by means of a pin 123A secured to the upper unit, and the other end is supported by a compression spring 127, the lower end of which is supported by a spring receiver 126 held by one end of a lever 125 rocking around a supporting point 124 fixed to the lower unit. With the upper and lower units being closed, the lever 123 is forcedly pushed up by the compression spring 127, which results in exerting pressure upon both the rollers 121 and 122. The left end of the lever 125 is engaging with a cam 131 rotated by a worm wheel 130 through a worm 129 driven by a stepping motor 128. Therefore, the compression spring 127 is compressed in accordance with an amount of projection of the cam 131 at an engaging point, which results in changing fixing pressure between both rollers. Adjustment of the fixing pressure may be made by manually turning a knob (not shown) which is operatively associated with either cam 131 or stepping motor 128. It is understood that in embodiments of the present invention fixing temperature and/or fixing pressure may be regulated to effect copying or printing of text and/or graphics on a support medium in a removable or permanent manner. In embodiments, the permanent fixing pressure may be any effective pressure to permanently fix the toned images, preferably about 95 psi or higher. In embodiments, the removable fixing pressure may be any effective pressure to removably fix the toned images, preferably from about 50 to about 80 psi, more preferably 55 to about 75 psi, and most preferably about 60 to about 70 psi.

It is contemplated that in embodiments of the present invention erasable toned images may be generated from originals which include bond paper, vellum paper, diazo blueline prints, sepias, original drawings, computer-generated plots, cut-and-tape composites, xerographic copies, rigid originals, and the like. The text and/or graphics to be printed or copied in a removable or permanent manner may also be in an electronic form. The support sheet which receives the removable or permanent toned images includes paper such as bond paper and vellum, and plastic such as polyester drafting film, transparencies, and the like. The support material may be any suitable size and thickness. It may also be packaged in any suitable form including sheets and rolls.

Various suitable resins may be selected for the toner compositions. Examples of suitable toner resins include crosslinked resins including crosslinked polyesters (reference for example copending U.S. Ser. Nos. 07/814,641 and 07/814,782, the disclosures of which are totally incorporated by reference), styrene acrylates, styrene methacrylates, polyimides, epoxies, diolefins, polyurethanes, vinyl resins, and polyesters, such as the polymeric esterification products of a dicarboxylic acid and a diol comprising a diphenol. Any suitable vinyl resin may be selected for the toner resins of the present application, including homopolymers or copolymers of two or more vinyl toohomers. Typical of such vinyl monomeric units include: styrene, p-chlorostyrene, vinyl naphthalene, unsaturated mono-olefins such as ethylene, propylene, butylene, and isobutylene; vinyl halides such as vinyl chloride, vinyl bromide, vinyl fluoride, vinyl acetate, vinyl propionate, vinyl benzoate, vinyl butyrate, and the like; vinyl esters such as esters of monocarboxylic acids including methyl acrylate, ethyl acrylate, n-butyl acrylate, isobutyl acrylate, dodecyl acrylate, n-octyl acrylate, 2-chloroethyl acrylate, phenyl acrylate, methylalphachloroacrylate, methyl methacrylate, ethyl methacrylate, and butyl methacrylate; acrylonitrile, methacrylonitrile, acrylimide; vinyl ethers, such as vinyl methyl ether, vinyl isobutyl ether, vinyl ethyl ether, and the like; vinyl ketones such as vinyl methyl ketone, vinyl hexyl ketone, methyl isopropenyl ketone and the like; vinylidene halides such as vinylidene chloride, vinylidene chlorofluoride and the like; and N-vinyl indole, N-vinyl pyrrolidene and the like. Also useful are styrene butadiene copolymers, Pliotone ®, available from Goodyear Company, and mixtures thereof. Particularly preferred in embodiments are a resin comprising poly-n-butylmethacrylate; a copolymer of styrene/butadiene which comprises 87 percent by weight of styrene and 13 percent by weight of butadiene; a copolymer of styrene/n-butylmethacrylate crosslinked with divinylbenzene 20–50% gel which comprises 50–60 percent by weight of styrene, 50–40 percent by weight of n-butyl methacrylate, and 0.1–0.3 percent by weight of divinylbenzene; and a copolymer of styrene/n-butyl methacrylate which comprises 50–60 percent by weight of styrene and 50–40 percent by weight of n-butyl methacrylate. The resin or resins are generally present in an amount of from about 30 to about 99 percent by weight of the toner composition, preferably from about 50 to about 99 percent by weight, and more preferably from about 70 to about 95 percent by weight, although they may be present in greater or lesser amounts.

Various suitable pigment particles can be employed in the toner compositions, including carbon black, like Regal 330 ®, magnetites comprised of a mixture of magnetic oxides, including the commercially available Mapico blacks, nigrosine dyes, colored pigments such as cyan, magenta, yellow, blue, green, brown, and the like, and mixtures thereof, with carbon black, such as Regal 330 ® carbon black, being the preferred colorant. These pigment particles are present in the toner composition in an amount of from about 3 percent by weight to about 20 percent by weight. When the pigment particles are magnetites, they are present in the toner composition in the amount of from about 2 percent by weight to about 70 percent by weight, and preferably in an amount of from about 3 percent by weight to about 25 percent by weight.

Suitable effective internal and external charge control additives can be incorporated into the toner compositions of the present invention, such as quaternary ammonium compounds, as disclosed in U.S. Pat. No. 4,937,157 and U.S. Pat. No. 4,904,762, the disclosures of which are totally incorporated by reference; alkyl pyridinium compounds, including cetyl pyridinium halides and cetyl pyridinium tetrafluoborates, as disclosed in U.S. Pat. No. 4,298,672, the disclosure of which is totally incorporated herein by reference; organic sulfate and sulfonate compounds, as disclosed in U.S. Pat. No. 4,338,390, the disclosure of which is totally incorporated herein by reference; and the like. Particularly preferred as a charge control agent is a quaternary ammonium salt selected from the group consisting of: dimethyldistearylammonium bisulfate; dimethyldistearylammonium methylsulfate; dimethyldistearylammonium sulfate; cetylpyridinium chloride; dimethyldistearylammonium hexafluorophosphate; and alkylammonium naphtholsulfonate. The charge enhancing additives are usually present in the final toner composition in an amount of from about 0.1 percent by weight to about 20 percent by weight.

The toner particles optionally may be formulated into a two-component developer by mixing with carrier particles. Various suitable carrier materials are selected for formulating the developer composition of the present invention providing that these carrier particles are capable of triboelectrically obtaining a charge of opposite polarity to that of the toner particles. Examples of these carriers include materials such as glass, steel, nickel, ferrites like copper and zinc, silicon dioxide and the like, with metallic carriers, especially magnetic carriers being preferred. These carriers can be used with or without a coating, examples of coatings including resins such as polystyrene, homopolymers, copolymers, and terpolymers; polymers of halogen containing ethylenes including vinyl fluorides, vinylidene fluorides, vinyl chlorides, vinylidene chlorides, chlorotrifluoroethylene, a vinyl chloride/chlorotrifluoroethylene copolymer, a vinyl chloride/vinyl acetate copolymer, a chlorotrifluoroethylene polymer, and various known vinyl chloride terpolymers. Acrylic polymers and copolymers typified by polymethylmethacrylate and siloxane polymers are also useful carrier coatings, particularly when negative charging toners are desired. Coated carrier particles with a diameter of, for example, from about 25 to about 1,000 microns, preferably about 40 to about 150 microns, can be selected providing these particles with sufficient density and inertia to avoid adherence to the electrostatic image during the development process. Many of the typical carriers that can be used are described in U.S. Pat. Nos. 2,618,441; 2,638,522; 3,533,835; 3,526,533; 3,590,000; 3,847,604; 3,767,598; 4,233,387; 4,935,326; and 4,937,166, the disclosures of which are totally incorporated by reference. The carrier particles can be mixed with the toner particles in various suitable combinations. Preferably, about 1 part per toner to about 10 parts to about 200 parts by weight of carrier are mixed.

It will be understood that various changes in the details, materials, steps and arrangements of parts which have been herein described and illustrated in order to explain the nature of the invention, will occur to and may be made by those skilled in the art upon a reading of this disclosure, and such changes are intended to be included within the principle and scope of this invention.

I claim:

1. A method for printing or copying characters on support medium in a removable manner to facilitate alternations comprising:
    (a) creating electrostatographically a first toned image, corresponding to the characters on a first support medium, wherein the image receiving side of the first support medium prior to receiving the first toned image is blank or contains extraneous markings;
    (b) fixing the first toned image to the first support medium by setting a first fixing condition efficacious to removably fix the first toned image, thereby rendering the first toned image removably fixed on the first support medium;
    (c) altering the first toned image by removing part of the first toned image thereby forming an altered image on the first support medium;
    (d) creating electrostatographically a second toned image, corresponding to the altered image, on a second support medium; and
    (e) fixing the second toned image to the second support medium by setting a second fixing condition efficacious to permanently fix the second toner image to the second support medium.

2. The method of claim 1, wherein steps (a) and (b) are accomplished in the same or different electrostatographic apparatus as used for steps (d) and (e).

3. The method of claim 1, wherein the first fixing condition comprises a fusing temperature lower than the fusing temperature of the second fixing condition.

4. The method of claim 1, wherein both the first and second support mediums are paper.

5. The method of claim 1, wherein the alteration step (c) is effected by erasing a portion of the toned image, marking the first support medium with a writing device, or erasing and marking in any sequence.

6. The method of claim 1, wherein the image receiving side of the first support medium prior to receiving the first toned image is blank.

7. The method of claim 1, wherein the extraneous markings are permanently affixed to the first support medium by letterpress, lithography, or gravure.

8. The method of claim 1, wherein the extraneous markings do not overlap with the first toned image.

9. The method of claim 1, wherein the first fixing condition comprises a fusing temperature of from about 40° C. to about 90° C.

10. The method of claim 1, wherein the first fixing condition comprises a fusing temperature of from about 40° C. to about 85° C. and the second fixing condition comprises a fusing temperature of from about 90° C. to about 200° C.

11. The method of claim 1, wherein the first fixing condition comprises a fusing temperature of from about 50° C. to about 70° C. and the second fixing condition comprises a fusing temperature of from about 100° C. to about 160° C.

12. The method of claim 1, wherein the first fixing condition comprises a fixing pressure of from about 50 to about 80 psi.

* * * * *